United States Patent
Zuluaga et al.

(10) Patent No.: US 6,654,630 B2
(45) Date of Patent: Nov. 25, 2003

(54) APPARATUS AND METHOD FOR THE OPTICAL IMAGING OF TISSUE SAMPLES

(75) Inventors: Andres F. Zuluaga, Boston, MA (US); Brett Bouma, Quincy, MA (US); Simon M. Furnish, Louisville, KY (US); Guillermo J. Tearney, Cambridge, MA (US); S. Eric Ryan, Hopkington, MA (US); Jing Tang, Allston, MA (US); Mark A. Griffin, Lexington, KY (US)

(73) Assignee: InfraReDx, Inc., Cambridge, MA (US)

(*) Notice: Subject to any disclaimer, the term of this patent is extended or adjusted under 35 U.S.C. 154(b) by 0 days.

(21) Appl. No.: 09/871,578

(22) Filed: May 31, 2001

(65) Prior Publication Data

US 2002/0183622 A1 Dec. 5, 2002

(51) Int. Cl.[7] .................................................. A61B 6/00
(52) U.S. Cl. ........................ 600/476; 600/473; 600/478; 600/407
(58) Field of Search ................................. 600/478, 477, 600/473, 476, 475, 407, 310, 109, 160, 182; 250/341, 462.1

(56) References Cited

U.S. PATENT DOCUMENTS

| | | | | |
|---|---|---|---|---|
| 4,987,884 A | * | 1/1991 | Nishioka et al. ............. 600/181 |
| 5,127,405 A | | 7/1992 | Alcala et al. | |
| 5,304,173 A | * | 4/1994 | Kittrell et al. ................ 606/15 |
| 5,425,117 A | * | 6/1995 | Miesak .......................... 385/33 |
| 5,773,835 A | * | 6/1998 | Sinofsky ................... 250/462.1 |
| 5,844,239 A | | 12/1998 | Kimura | |
| 6,119,031 A | | 9/2000 | Crowley | |
| 6,134,003 A | * | 10/2000 | Tearney et al. .............. 356/450 |
| 6,238,348 B1 | * | 5/2001 | Crowley et al. ............. 600/476 |
| 6,485,413 B1 | * | 11/2002 | Boppart et al. .............. 600/160 |
| 6,564,088 B1 | | 5/2003 | Soller et al. ................. 600/478 |
| 2002/0183623 A1 | * | 12/2002 | Tang et al. ................... 600/476 |

* cited by examiner

Primary Examiner—George Manuel
Assistant Examiner—Barry Pass
(74) Attorney, Agent, or Firm—Fish & Richardson P.C.

(57) ABSTRACT

A catheter based optical system for generating data as to the condition of a tissue sample of a mammalian vessel. The system includes an elongated catheter shaft having a tissue engaging distal end and a coupled proximal end and an elongated optical delivery fiber arrangement disposed through a lumen of said catheter, said optical delivery fiber arrangement having a distal end and a proximal end. The distal end of the delivery fiber arrangement has a re-director light emitter thereon for directing light against mammalian tissues. An elongated optical collection fiber arrangement is disposed through a lumen of the catheter, the optical collection fiber arrangement having a distal end and a proximal most end. The distal end of the collection fiber arrangement has a re-director light receiver thereon for receiving light reflected from the mammalian tissue by the light emitter. The light emitter and the light receiver are longitudinally spaced apart from one another in the distal end of the catheter. The catheter apparatus includes a light source in communication with the delivery fiber and a signal detector in communication with the receiving fiber for receiving and presenting data collected.

39 Claims, 6 Drawing Sheets

APPARATUS AND METHOD FOR THE OPTICAL IMAGING OF TISSUE SAMPLES

FIELD OF THE INVENTION

This invention relates to catheters and more particularly to catheter apparatus utilizing optical imaging arrangements for the sensing and analysis of tissue or particulate samples in a medium.

BACKGROUND OF THE INVENTION

Mammalian vessels are subject to damage by atherosclerotic plaque, vascular lesions, and aneurysms. Such plaque may be simple plaque or vulnerable plaque. Vulnerable plaque consists of lipid-rich core material and inflammatory cells. These vulnerable plaques are prone to rupture and erosion. Sixty to seventy percent of fatal myocardial infarctions are triggered by plaque rupture. In about twenty five to thirty percent of fatal infarctions, plaque erosion or ulceration is the triggering mechanism. Erosion occurs when the endothelium beneath the thrombus is replaced by inflammatory cells. Such inflammatory cells are commonly associated with plaque rupture and ulceration. Plaque rupture and ulceration may respond to and aggravate intimal injury, promoting thrombosis and vasoconstriction.

Vulnerable plaques, which pose a significant risk of precipitating infarction, occur in coronary arteries which may appear apparently normal or only mildly stenotic on angiograms. Thus, detection of these vulnerable plaques prior to any rupture or erosion would present a significant advance in the treatment of a mammalian patient.

BRIEF SUMMARY OF THE INVENTION

The present invention relates to a catheter based system for the optical analysis of mammalian vessels, tissue samples and methods of utilization of that catheter based system. Such a catheter based system is utilized to independently deliver and collect optical radiation through an arrangement of optical fibers in such a manner that the radiation delivered and collected by those optical fibers is known and may be controlled.

The catheter based optical system of the present invention comprises a light source such as a laser or the like, for example a titanium sapphire laser in optical communication with an optical coupler. The catheter based optical system includes and elongated catheter having a distal end and a proximal end. The catheter comprises an outermost sheath of thin resilient material having proper columnar strength, the distal end of which is formed of polyethylene or other biocompatible material, and is optically transparent. An elongated optical delivery fiber arrangement is disposed from the proximal end of the catheter through and into the distal end thereof. An optical collection fiber arrangement is also disposed within the catheter sheath alongside the optical delivery fiber arrangement. The optical delivery fiber arrangement has a distal end which is in optical communication with an optical re-director within the distal end of the catheter sheath. The optical delivery fiber arrangement has a proximal end which is in optical communication with the optical coupler at the proximal end of the catheter shaft. The optical collection fiber arrangement has a distal end which is in optical communication with the optical re-director within the distal end of the catheter sheath. The optical collection fiber arrangement has a proximal end which is in optical communication with the optical coupler at the proximal end of the catheter sheath. The optical re-director at the distal end of the catheter sheath is arranged to re-direct light traveling through the optical delivery fiber arrangement and generally radially outwardly through the sidewall of the catheter sheath, and onto a vessel wall of a mammalian subject undergoing the test procedure.

A reflected light path receiving member may be arranged in the optical re-director a spaced distance apart from the optical delivery path within the optical re-director. The receiving member collects the reflected light from any tissue within the mammalian vessel and communicates it proximally through the optical collection fiber arrangement for transmission into the optical coupler.

A detector is in communication with the optical coupler, to receive the optical radiation from the optical collector fiber arrangement and convert that signal into an electronic display. The electronic display is presented as an analysis of the tissue structure within the vessel being examined within the mammalian host.

In a further embodiment of the present invention, a rotatable optical coupler is arranged in optical communication between the optical coupler and the proximal ends of the optical delivery fiber arrangement and the optical collection fiber arrangement. The rotatable optical coupler, in this embodiment, may be configured as an optical slip ring generally somewhat similar to those arrangements as may be seen in U.S. Pat. No. 4,109,998 to Iverson or in U.S. Pat. No. 4,725,116, to Spencer et al. or to U.S. Pat. No. 4,872,737, to Fukahori et al., each of which patents are incorporated herein by reference in their entirety. In this embodiment, both the optical delivery fiber arrangement and the optical collection fiber arrangement are each rotated simultaneously about an elongated axis of rotation which is co-axial with the longitudinal axis of the catheter sheath. In this embodiment, the optical re-director also rotates within the distal end of the catheter sheath.

The optical re-director may be comprised of right angled extensions or of diagonally arranged mirrors disposed at the distal end of each respective optical collection fiber arrangement and optical delivery fiber arrangement. The distal end of each fiber arrangement respectively emits and collects optical radiation in an independent and separate manner with respect to the inner wall of the vessel of the mammalian patient into which the catheter apparatus is being worked. The distal ends of each fiber arrangement are spaced apart from one another along the longitudinal axis of rotation of the fiber assembly. The use of independent fibers for delivering and for collecting optical radiation permits control of the separation between where the point of the optical radiation impinges upon the tissue sample of the vessel and the point where the optical radiation is collected from the tissue sample of the vessel. Such an optical fiber arrangement may be in the order of two to three microns in diameter to as much as two to three millimeters in diameter. In a further contemplative embodiment, the optical delivery fiber arrangement may be comprised of a plurality of individual elongated optical fibers which collectively comprise the optical delivery fiber arrangement. In a similar manner, the optical collection fiber arrangement may be comprised of a plurality of individual optical collection fibers.

In a further preferred embodiment of the present invention, the optical collection fiber arrangement may be of a different, i.e. a greater diameter than the optical delivery fiber arrangement to permit weaker signals to be transmitted therethrough without loss of a signal strength.

In yet a further object of the present invention, it is contemplated that the optical delivery fiber arrangement and the optical collection fiber arrangement be in a coil with respect to one another. That is, the delivery fiber arrangement may be arranged as an inner coil twisted in a one hand direction with the collection fiber arrangement disposed as an outer coil of an opposite hand direction or as a twisted pair, to provide columnar strength to the catheter sheath during its insertion within the mammalian vessel, and to provide stability while permitting the minimization of the diameter of the catheter sheath that would otherwise require wall reinforcement and reinforced guideability.

In a further embodiment of the present invention, the optical delivery fiber arrangement and the optical collection fiber arrangement may be coaxial, and separated by a reflecting or containing cladding arranged therebetween. A containing cladding may also be arranged on the outer peripheral surface of the combined delivery fiber and collection fiber arrangement arranged rotatably within the catheter sheath. Such an embodiment may include the delivery fiber arrangement comprising the inner core of the collective optical fiber arrangement assembly. Such a coaxial fiber arrangement would be in optical communication with an optical slip ring coupler arrangement wherein an inner or outer fiber arrangement acts as the delivery medium and the outer or inner fiber arrangement acts as the collection fiber arrangement for transmission to a detector for conversion to a proper electrical signal for analysis of the mammalian vessel wall.

Thus the invention comprises a catheter based optical system for generating data as to the condition of tissue of a mammalian vessel, comprising an elongated catheter shaft having a tissue engaging distal end and a coupled proximal end. An elongated optical delivery fiber is arranged through a lumen of the catheter. The optical delivery fiber arrangement has a distal end and a proximal end. The distal end of the delivery fiber arrangement has a re-director light emitter thereon for directing light against the mammalian tissues. An elongated optical collection fiber arrangement is also disposed through a lumen of the catheter, the optical collection fiber arrangement having a distal end and a proximal end. The distal end of the collection fiber arrangement has a re-director light receiver thereon for receiving light reflected from the mammalian tissue by the light emitter. The light emitter and the light receiver are longitudinally spaced apart from one another in the distal end of the catheter. The catheter apparatus includes a light source in communication with the delivery fiber and a signal detector in communication with the receiving fiber for receiving and presenting the data collected. The elongated delivery fiber arrangement and the elongated collection fiber arrangement may rotate about a common longitudinal axis within the elongated catheter shaft. The delivery fiber arrangement may be of a different diameter than the diameter of the collection fiber. The catheter apparatus may include a rotary optical coupler arranged between the light source and the delivery fiber arrangement. The rotary optical coupler may also be arranged between the collection fiber arrangement and the signal detector. The delivery fiber arrangement and the collecting fiber arrangement may form a coiled pair. The delivery fiber arrangement may be comprised of a plurality of individual delivery fibers. The collection fiber arrangement may be comprised of a plurality of individual collection fibers. The light emitter at the at distal end of the delivery fiber arrangement may include a rotary optical coupler arranged to direct light from the delivery fiber arrangement to the tissue and to direct light reflected from the tissue into the collection fiber arrangement. The rotary optical coupler may comprise a beam splitter. The delivery fiber arrangement and the receiving fiber arrangement may be co-axially arranged with respect to one another. The delivery fiber arrangement and the receiving fiber arrangement may be separated by a containing cladding arranged therebetween. The delivery fiber arrangement and the receiving fiber arrangement may be longitudinally enclosed by a containing cladding.

The invention may also include a method of generating data as to the condition of tissue of a mammalian vessel by a catheter based optical system comprising the steps of: arranging an elongated catheter shaft having a tissue engaging distal end and a coupled proximal end in a mammalian vessel to be examined; placing an elongated optical delivery fiber arrangement through a lumen of the catheter, the optical delivery fiber arrangement having a distal end and a proximal end; the distal-most end of the delivery fiber arrangement having a re-director light emitter thereon for directing light against the mammalian tissues; arranging an elongated optical collection fiber arrangement through a lumen of the catheter, the optical collection fiber arrangement having a distal end and a proximal end, the distal end of the collection fiber arrangement having a re-director light receiver thereon for receiving light reflected from the mammalian tissue by the light emitter; the light emitter and the light receiver may be longitudinally adjustably spaced apart from one another in the distal end of the catheter; and connecting a light source into optical communication with the delivery fiber arrangement and a signal detector in communication with the receiving fiber arrangement for receiving and presenting data collected. The method may include the steps of: rotating the collection fiber arrangement and the delivery fiber arrangement about a common axis within the catheter; connecting the collection fiber arrangement and the delivery fiber arrangement to an optical slip ring for communication of optical signals sent from the light source and returned to the detector for presentation and analysis thereof; and twisting the delivery fiber arrangement and the collection fiber arrangement into a coil about one another.

The invention also includes a method of generating data as to the condition of tissue of a mammalian vessel by a catheter based optical system comprising the steps of: inserting an elongated optical delivery fiber and a separate elongated collection fiber into the catheter, each of the fibers having a proximal and a distal end, each distal end of each of the fibers having a light re-director thereon; attaching a rotary optical pickup to the proximal ends of each of the fibers in the catheter so as to be in optical communication therewith; attaching a light source to the rotary optical pickup so that the light source is in light communication with the light redirectors at the distal end of the fibers; inserting the catheter into a mammalian vessel; energyzing the light source to provide light through the delivery fiber to the re-director and onto the tissue; reflecting the light from the tissue into the re-director on the distal end of the collection fiber; receiving the reflected light through the rotary pickup; and directing the received light into a signal detector for analysis of mammalian tissue thereby. The method may include the step of rotating the delivery fiber and the collection fiber about a common axis so as to permit a circumferential scan of mammalian tissue in the vessel. The method may include the step of spacing the re-directors apart by a longitudinal distance within the catheter to effect reflection characteristics of the light collected. The method may include the step of adjusting the longitudinal distance apart of the redirectors by an adjustment arrangement at the proximal end of the catheter. The method may also include he step of: placing one of the optical fibers within the other of the fibers so as to effect a co-axial arrangement therebetween. The method may include the step of: placing a containment layer between the optical fibers to prevent optical light exchange therebetween.

It is an object of the present invention to provide an improvement in the recognition and treatment of vulnerable plaque in mammalian systems over that which has been shown in the prior art.

It is a further object of the present invention to provide a catheter based system for the optical analysis of mammalian vessels.

It is yet a further object of the present invention to provide a fiberoptic arrangement within a catheter system which may be adaptable for individual vessel analysis.

It is still yet a further object of the present invention to provide a catheter based optical analysis of mammalian vessels when fiberoptic components are utilized to facilitate the positioning of the catheter apparatus.

BRIEF DESCRIPTION OF THE DRAWINGS

The objects and advantages of the present invention will become more apparent when viewed in conjunction with the following drawings, in which.

DESCRIPTION OF THE PREFERRED EMBODIMENTS

Figure 1:
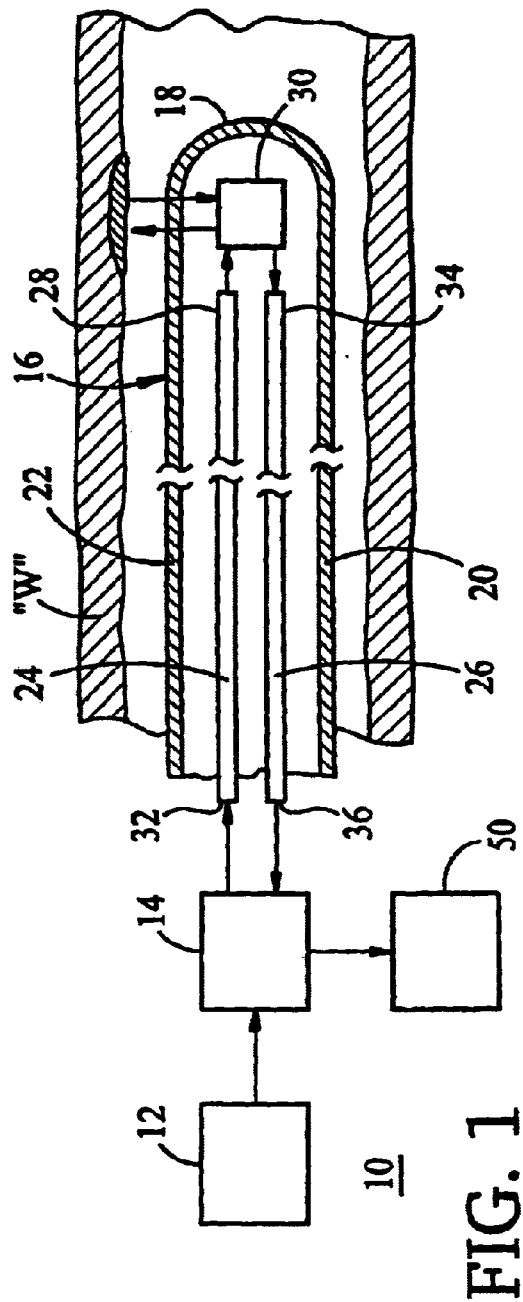
FIG. 1 is a view part in block diagram and part in a sectional elevation, of a catheter in a vessel.

Referring now to the drawings in detail, and particularly to FIG. 1, there is shown the present invention which comprises a catheter based optical system 10 for the optical analysis of mammalian vessels and methods of utilization of that catheter based apparatus. Such a catheter based optical system 10 is utilized to independently deliver and collect optical radiation through an arrangement of optical fibers in such a manner that the radiation delivered and collected by those optical fibers is known and may be controlled.

The catheter based optical system 10 of the present invention comprises a light source 12 such as a laser or the like, for example a titanium sapphire laser preferably with a power of about 5 milliwatts and being in optical communication with an optical coupler 14, such as for example an optical circulator. The catheter based optical system 10 includes an elongated catheter 16 having a distal end 18 and a proximal end 20, as may be seen in FIGS. 1 and 2. The catheter 16 comprises an outermost sheath 22 of thin resilient material providing proper columnar strength, the distal end of which may be formed of polyethylene or any other biocompatible material, and is optically transparent.

An elongated optical delivery fiber arrangement 24 is disposed from the proximal end 20 of the catheter 16 through and into the distal end 18 thereof, as may be seen in the figures. An optical collection fiber arrangement 26 is also disposed within the catheter sheath 22 alongside the optical delivery fiber arrangement 24. The optical delivery fiber arrangement 24 has a distal end 28 which is in optical communication with an optical re-director 30 within the distal end 18 of the catheter sheath 22. The optical delivery fiber arrangement 24 has a proximal end 32 which is in optical communication with the optical coupler 14 at the proximal end 20 of the catheter shaft 16. The optical collection fiber arrangement 26 has a distal end 34 which is in optical communication with the optical re-director 30 within the distal end 18 of the catheter sheath 22. The optical collection fiber arrangement 26 has a proximal end 36 which is in optical communication with the optical coupler 14 at the proximal end 20 of the catheter sheath 22. The optical re-director 30 at the distal end 18 of the catheter sheath 22 is arranged to re-direct light traveling through the optical delivery fiber arrangement 24 and 26 and generally radially outwardly through the sidewall of the catheter sheath 22, and onto a vessel wall "W" of a mammalian subject undergoing the test procedure.

Figure 3:
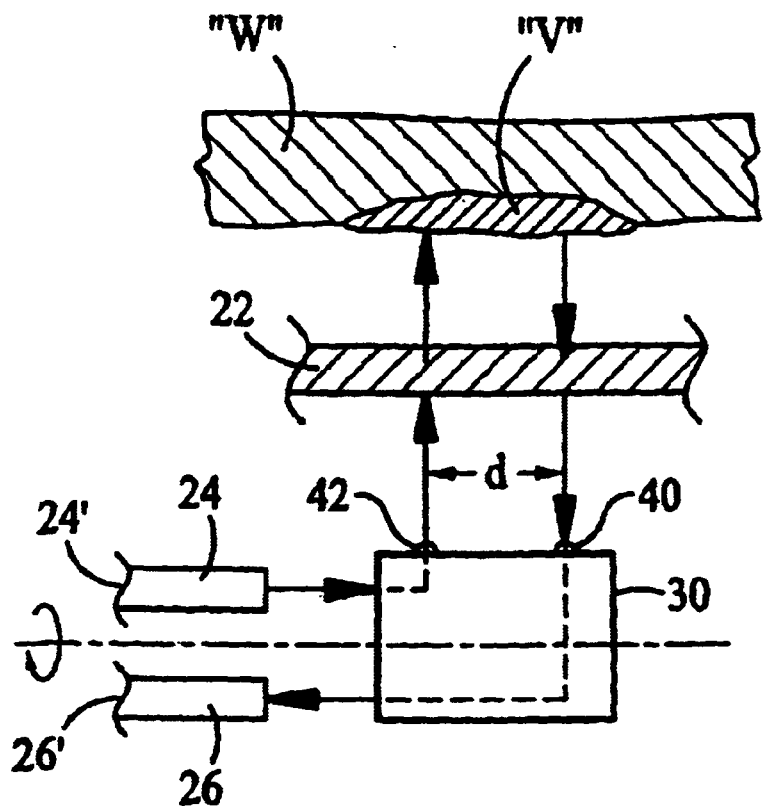
FIG. 3 is an enlarged view of an optical re-director arranged within the distal end of the catheter sheath.
Figure 4:
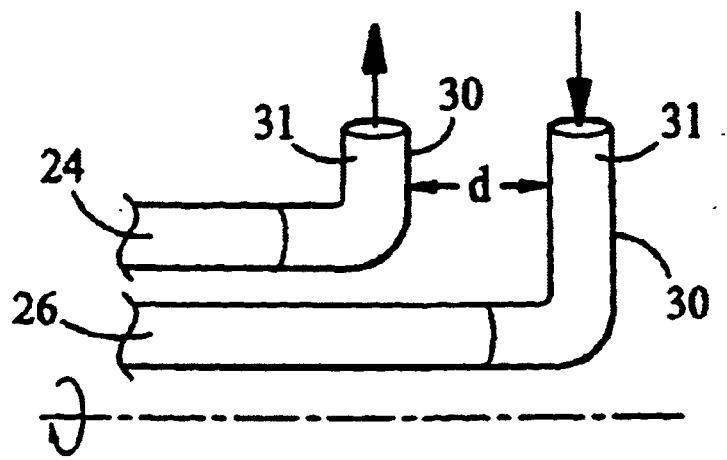
FIG. 4 is a further view of the embodiment of the optical re-director shown in FIG. 3.

A reflected light path receiving member 40 may be arranged in the optical re-director 30 a spaced distance apart "d" from the optical delivery lens 42 within the optical re-director 30, as may be seen in FIGS. 3 and 4. The receiving lens 40 collects the reflected light "L" from any tissue such as vulnerable plaque "V" within the mammalian vessel and communicates it proximally through the optical collection fiber arrangement 26 for transmission into the optical coupler 14.

Figure 2:
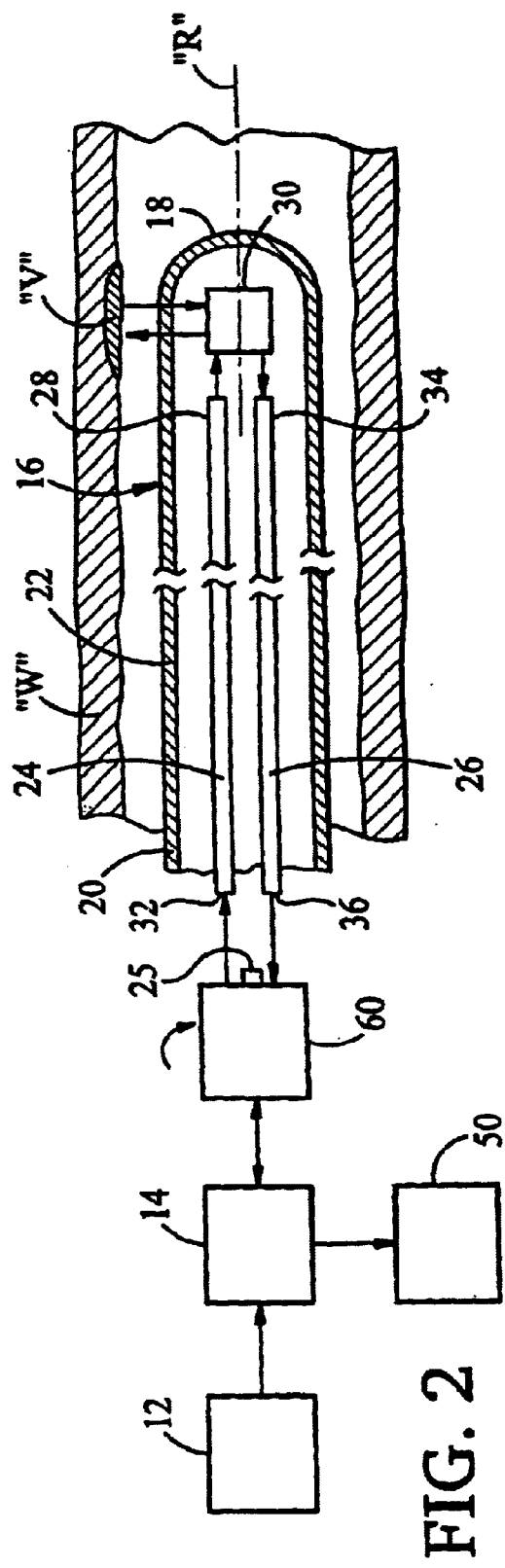
FIG. 2 is a view similar to FIG. 1, showing a further embodiment thereof.

A detector 50 is in communication with the optical coupler 14, as shown in FIGS. 1 and 2, to receive the optical radiation from the optical collector fiber arrangement 26 and convert that signal into an electronic display on the detector 50. The electronic display is presented as an analysis of the tissue structure within the vessel wall "W" being examined within the mammalian host.

In a further preferred embodiment of the present invention, a rotatable optical coupler 60 is arranged in optical communication between the optical coupler 14 and the proximal ends 32 and 36 of the optical delivery fiber arrangement 24 and the optical collection fiber arrangement 26 respectively, as shown in FIG. 2. The rotatable optical coupler 60, in this embodiment, may be comprised of an optical slip ring. In this embodiment, both the optical delivery fiber arrangement 24 and the optical collection fiber arrangement 26 are each rotated simultaneously about an elongated axis of rotation "R" which is co-axial with the longitudinal axis of the catheter sheath. In this embodiment, the optical re-director 30 also rotates within the distal end 18 of the catheter sheath 22, although in certain embodiments, the re-director 30 (such as a conical mirror arrangement) may be stationary within the catheter sheath 22.

The optical re-director 30 may be comprised of right angled extensions 31, as shown in FIG. 3, or of diagonally arranged mirrors, (not shown for clarity), disposed within the re-director 30 at the distal end of each respective optical collection fiber arrangement 26 and optical delivery fiber arrangement 24. The distal end of each fiber arrangement 28 and 34 respectively emits and collects optical radiation in an independent and separate manner with respect to the inner wall of the vessel "W" of the mammalian patient into which the catheter apparatus 10 is being worked. The distal ends of each fiber arrangement are spaced apart from one another along the longitudinal axis of rotation of the fiber assembly as may be seen in FIGS. 3 and 4. The use of independent fibers 24 and 26 for delivering and for collecting optical radiation permits control of the separation between where the point of the optical radiation impinges upon the tissue sample of the vessel and the point where the optical radiation is collected from the tissue sample of the vessel. Such fibers 24 and 26 may be variably spaced apart from one another by an adjustor 25 to effect longitudinal or angular spacing therebetween. Such an optical fiber arrangement may be in the order of two to three microns in diameter to as much as two to three millimeters in diameter.

In a further contemplative embodiment, the optical delivery fiber arrangement 24 may be comprised of a plurality of individual elongated optical fibers 24' which collectively comprise the optical delivery fiber arrangement. In a similar manner, the optical collection fiber arrangement 26 may be comprised of a plurality of individual optical collection fibers 26' as represented in FIG. 3. In a further preferred embodiment of the present invention, the optical collection fiber arrangement 26 may be of a different, i.e. a greater diameter than the optical delivery fiber arrangement 24 to permit weaker signals to be transmitted therethrough without loss of a signal strength.

Figure 5:
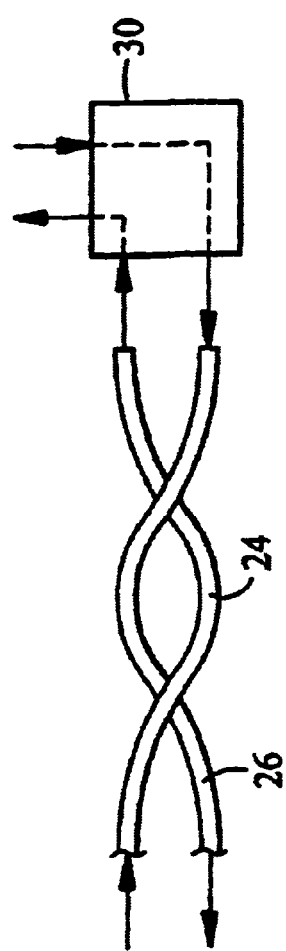
FIG. 5 is a side elevational view of a further embodiment of the delivery and collection fiber arrangement for the present catheter assembly.

A further object of the present invention contemplates that the optical delivery fiber arrangement 24 and the optical collection fiber arrangement 26 be in a coil with respect to one another, as may be seen in FIG. 5. Further, the delivery fiber arrangement may be arranged as an inner coil twisted in a one hand direction with the collection fiber arrangement disposed as an outer coil of an opposite hand direction or as a twisted pair, to provide columnar strength to the catheter sheath 22 during its insertion within the mammalian vessel, and to provide stability while permitting the minimization of the diameter of the catheter sheath 22 that would otherwise require wall reinforcement and reinforced guideability.

Figure 7:
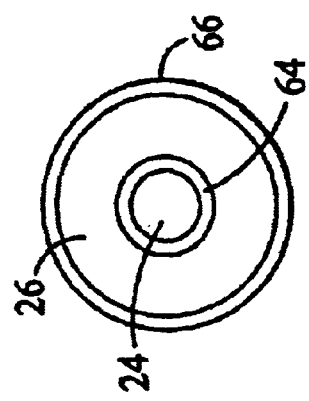
FIG. 7 is a cross sectional view of the optical fiber arrangement shown in FIG. 6.
Figure 6:
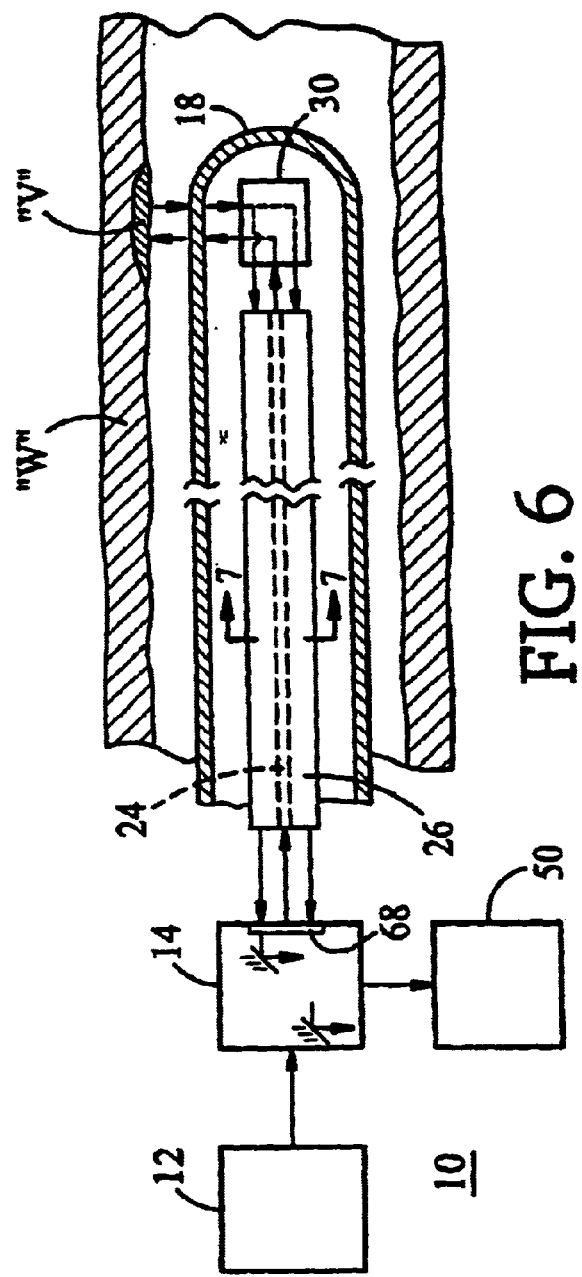
FIG. 6 is a view similar to FIG. 1 showing a further embodiment of the optical fiber arrangement.

The optical delivery fiber arrangement 24 and the optical collection fiber arrangement 26 may be coaxial as a yet further preferred embodiment of the present invention, and separated by a containing cladding 64 arranged therebetween, as may be seen in FIGS. 6 and 7. A reflective or containing cladding 66 may also be arranged on the outer peripheral surface of the combined delivery fiber and collection fiber arrangement arranged rotatably within the catheter sheath 22. The containing cladding may be comprised of for example, a plastic polymer such as teflon. Such an embodiment may include the delivery fiber arrangement comprising the inner core of the collective optical fiber arrangement assembly. Such a co-axial fiber arrangement would be in optical communication with an optical slip ring coupler arrangement 68 wherein an inner or outer fiber arrangement acts as the delivery medium and the outer or inner fiber arrangement acts as the collection fiber arrangement through a transmission to a detector for conversion to a proper electrical signal for analysis of the mammalian vessel wall.

Figure 8:
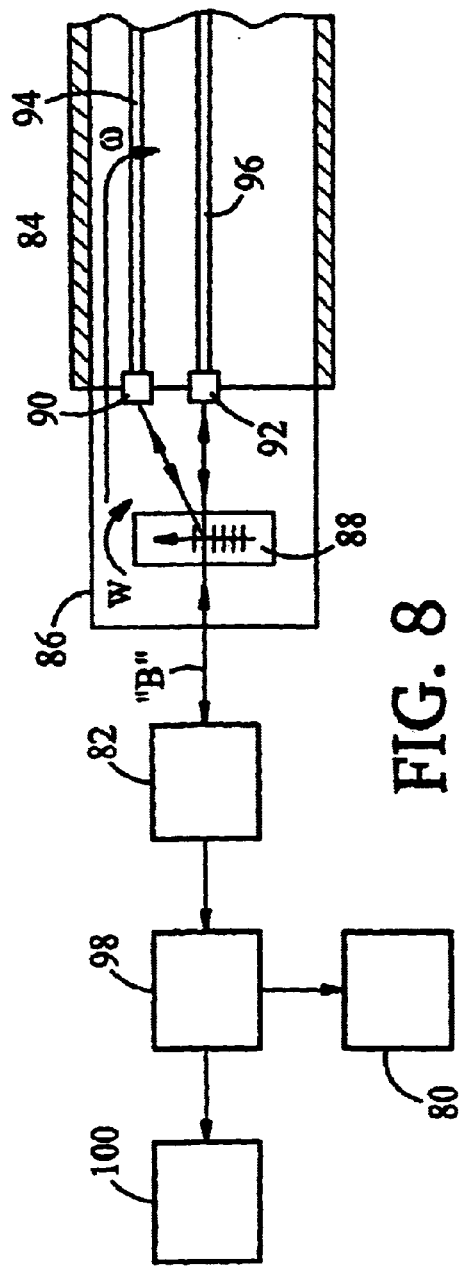
FIG. 8 is a is a view part in block diagram and part in sectional elevational view of a catheter with a further embodiment of an optical coupler therewith, showing the components of the system.

In a further embodiment of the catheter based optical system 10 of the present invention, as is shown in FIG. 8, a light source 80 directs light energy to an optical beam connecting element 82 which itself directs its light into the catheter 84 through a rotary optical coupler 86. The rotary optical coupler 86 is comprised of an acousto-optic modulator 88 and a first and a second fiber coupling element 90 and 92 such as for example, lenses and mirrors. The acousto-optic modulator 88 is arranged such that one half of the light input intensity is directed through the fiber coupling element 90 to the first optical fiber 94, and the other half of the light input intensity is directed through the second fiber coupling element 92 to the second optical fiber 96. Splitting the light input into at least two optical fibers 90 and 96 as indicated in this embodiment maximizes the overall throughput of the desired signal. Other splitting ratios will improve efficiency, although not quite as well as that of the present embodiment. This split light path permits the differentiation of the light that has been delivered by one optical fiber and collected by the other optical fiber from light that has been delivered and collected by the same fiber. This happens when light is deflected by an acousto-optic modulator 88, because it changes its optical frequency by an amount equal in magnitude to the acoustic frequency (va) utilized in the acousto-optic modulator 88. The change in frequency is positive when the deflection is in the same direction as the direction of acoustic propagation in the crystal of the acousto-optic modulator 88, that is the path of light from the optical beam connecting element 82 to the acousto-optic modulator 88 to the fiber coupling element 90 then to the first optical fiber 94. The frequency shift is negative when the deflection is in a direction opposite that of acoustic propagation in the acousto-optic modulator 88, which is the path from the first optic fiber 94 to the acousto-optic modulator 88 and back to the optical beam connecting element 82. Light that is not deflected is not affected by a change in frequency such as light traveling from the optical beam connecting element 82 through the acousto-optic modulator 88 and into the second coupling element 92 and hence into the second optical fiber 96, and similarly, light traveling on a return path through the second optical fiber 96 to the second coupling element 92 and through the acousto-optic modulator 88, and into a wavelength selective device 98 such as a spectograph or optical filter and into the detector 100 will likewise be unaffected in frequency. Light however that is deflected in one direction but not in the other direction will have a net shift in frequency, either positive via a path from the acousto-optic modulator 88 to the first coupling element 90 to the first optic fiber 94 and returning on the second optical fiber 96 (as a collection fiber) to the second coupling element 92 through the acousto-optical modulator 88 or by a negative via a path from the acousto-optical modulator 88 to the second coupling element 92 to the second optical fiber 96 and returning from the reflection off of the vulnerable plaque and through the first optical fiber 94 to the first coupling element 90 and through the acousto-optical modulator 88. Light that is both delivered and collected by the second optical fiber 96 has no frequency shift during either delivery to a vulnerable plaque examination site or collection from a vulnerable plaque examination site. Light that is delivered to an examination site and collected from an examination site by the first optical fiber 94 acquires a positive shift in the delivery of light to the examination site and acquires a negative shift in the collection path from the examination site, resulting in a net zero shift. The rotary optical coupler 86 and the optical fibers 94 and 96, as well as the first and second coupling elements 90 and 92 are fixed with respect to one another and hence correspondingly rotate with one another within the catheter 84 at an angular speed "w" about an axis of rotation "P" which corresponds to the axis of the optical beam "B" communicating between the optical beam connecting member 82 and the rotary optical coupler 86. This axis is such that the Bragg condition is met for the acousto-optical modulator 88 at all rotational positions. Light returning within the catheter 84 is then routed through the rotary optical coupler 86 and the optical beam connecting element 82 and through the wavelength selective device 98 and the detector 100 where the optical signal is processed into an electrical signal. The optical beam connecting member 82 may also be wavelength insensitive, such as if it were a circulator or a broadband beamsplitter. In the instance of this embodiment where the optical beam connecting member 82 is a circulator, the system would appreciate its greatest efficiency, since a broadband beamsplitter would only be about 25% efficient in the case where reflection and transmission are equal. The optical beam connecting element 82 may also be wavelength sensitive, taking advantage of the frequency shift impressed in the desired signal returning from the catheter 84. Examples here would be holographic or dielectric coating notch mirrors. The desired property is the reflection of the input wavelength (frequency) with transmission of the returned, frequency shifted wavelengths. Since the frequency shift impressed by the acousto-optic modulator 88 is very small, very stringent requirements are needed for notch mirrors. Currently, holographic elements are favored than dielectric coating elements.

When the optical beam connecting member 82 is wavelength insensitive, a means of differentiating the wavelengths of the returning signals is needed and provided by the wavelength selective device 98. Such wavelength selective device 98 has to permit of only frequency-shifted signals. Such a wavelength selective device 98 may be comprised of holographic and dielectric filters, Bragg gratings, etalons and monochromators.

Figure 9:
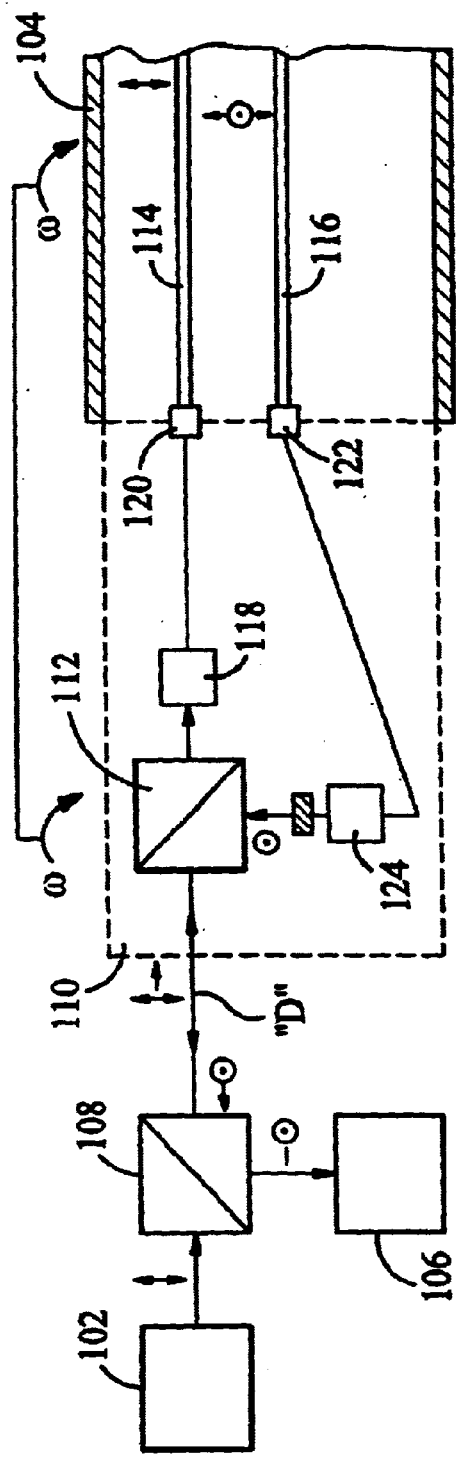
FIG. 9 is a view part in block diagram and part in sectional elevational view of a catheter with another further embodiment of an optical coupler therewith, showing the components of the system.

A further embodiment of the optical coupler arrangement is shown in FIG. 9. This particular arrangement makes use of a pair of polarizing beamsplitters to preferentially direct light from the light source 102 to the catheter 104, and directs the returning light from the catheter 104 to the detector 106. The elements of this embodiment of the rotary coupling include the following: The polarized source 102 is directed toward a first polarizing beamsplitter 108, which is preferably oriented such that the source's polarization is transmitted maximally. The light signal is then caused to enter the rotary optical coupler 110 where a second polarization beamsplitter 112 then directs the light beam into a first and a second optical fiber 114 and 116 through an arrangement of optical elements 118, 120, 122 and 124. The light beam returning from the catheter 104 goes through the rotary optical coupler 110 and is reflected by the first polarizing beamsplitter 108 into the detector 106. The optical coupler 110 and the rotating catheter elements (incl. optical fibers 114 and 116 and beamsplitter 112) are fixed with respect to each other and rotate at angular speed "w". The optical beam "D" connecting polarizing beam splitters 108 and 112 defines the axis of rotation.

This design preferentially detects light that has traveled toward the tissue sample (ie. vulnerable plaque) in one of the optical fibers 114 or 116 and returned in the other optical fiber 116 or 114 in the manner exemplified in FIG. 9. The light source 102 is polarized in the p plane, (the plane of the paper), and the first polarizing beamsplitter 108 is arranged such that the p polarization is maximally transmitted. The second polarizing beamsplitter 112 is also set up as shown in FIG. 9, such that the p polarization is also maximally transmitted and sent through the optical elements 118 and 120 to the first optical fiber 114. The light is specularly reflected by the tissue sample and coming back into the first optical fiber 114 will retain its p polarization and will be transmitted by the polarizing beamsplitters 112 and 108. The light that has multiply scattered and is collected by the distal end of the second optical fiber 116 will be depolarized and as such will have a significant s polarization component. This s component will be reflected by the first and second polarizing beamsplitters 108 and 112 and then directed to the signal detector 106 where the optical will be converted into an electrical signal. The p component returned by second optical fiber 116 from its distal collector arrangement will be transmitted by the second polarizing beamsplitter 112 and will thus not reach the signal detector 106. When the rotary optical coupler 110 and the rotating catheter elements are at an angular position that is 90 degrees from that depicted, the roles of the first and secvond optical fibers 114 and 116 are reversed. That is the second fiber 116 acts as a delivery fiber and the first optical fiber 114 acts as a collection fiber. At angular positions between zero shown in the diagram and 90 degrees, the first and second optical fibers114 and 116 act as both delivery and collection means, but the setup still discriminates between the input p polarization and the exiting S polarization, a process that can only take place by the light that has been depolarized by traveling between different optical fibers 114 and 116 and through the tissue sample (multiple scattering). Since this device relies on polarization, the use of polarization maintaining optical fibers at 114 and 116 is needed.

Figure 10:
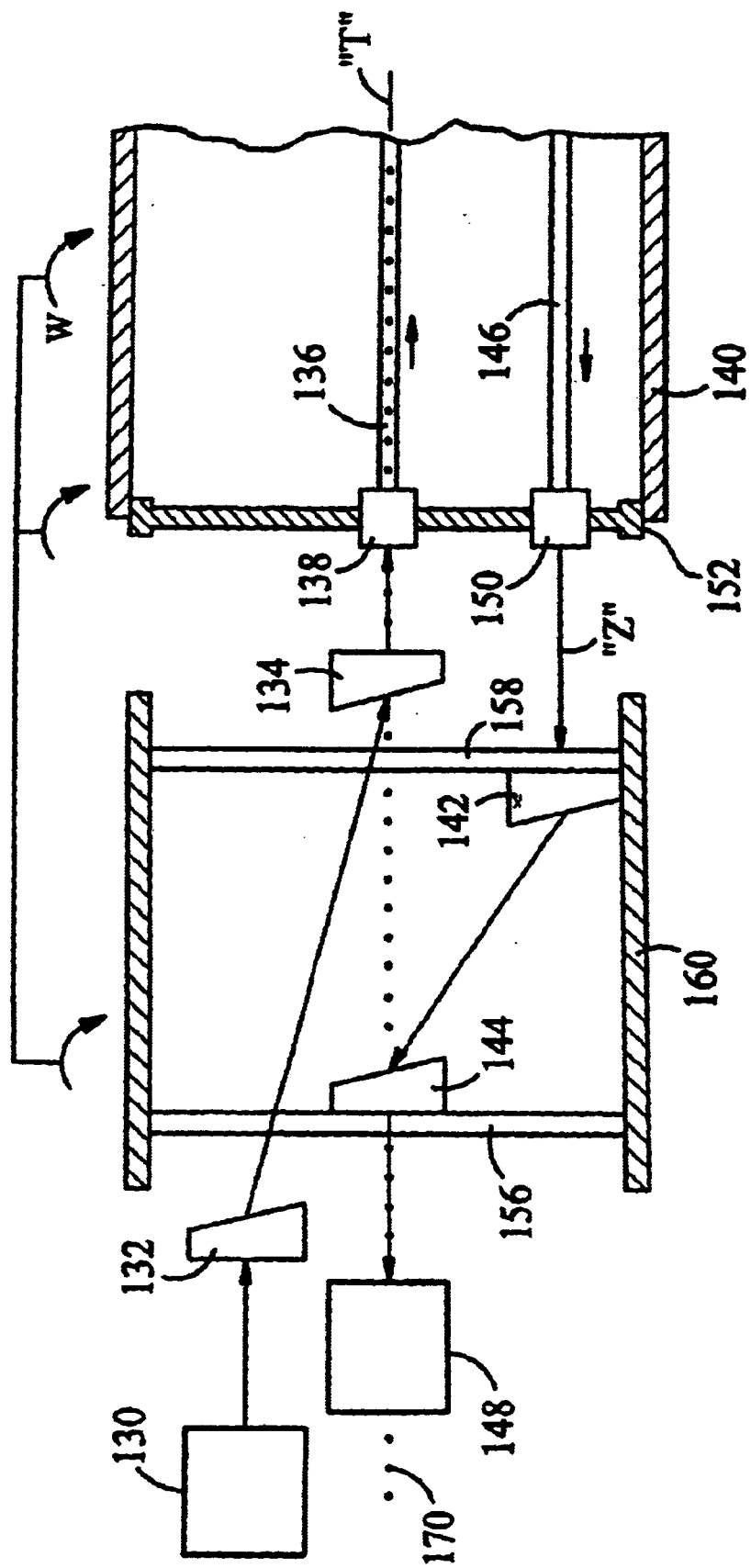
FIG. 10 is a view part in block diagram and part in sectional elevational view of a catheter with yet another further embodiment of an optical coupler therewith, showing the components of the system.

A yet still further embodiment of the optical coupler arrangement for the catheter based optical system 10 of the present invention is shown in FIG. 10 where the input beam and the output beams are not co-linear across the junction between the stationary and rotary components thereof. The light beam from the light source 130 is deflected by a first and a second wedge delivery prisms 132 and 134 and is coupled into a first optical delivery fiber 136 by an optical fiber coupling element 138. Light returning through the catheter 140 from its reflection at the site of body tissue being examined at the distal end of the catheter 140 (not shown for clarity), is deflected by wedge collection prisms 142 and 144 after collection by and passage through the optical collection fiber 146. The beam of light "Z" is then directed towards the signal detector 148. The wedge prisms 142 and 144 are each mounted on a transparent window 156 and 158, which in turn are mounted on a rotary mount 160. The optical fiber coupling elements 138 and 150 (i.e. an arrangement of lenses/mirrors) are arranged on a rotary mount 152. The rotary mounts 152 and 160 and the rotating optical fiber 136 and 146 and their respective optical fiber coupling elements 138 and 150 are all fixed with respect to one another and rotate at an angular speed "w". The axis of rotation "T" is defined by the dotted line 170. In this particular embodiment of the optical coupler arrangement, the direction of the light beam may be reversed, exchanging positions of the light source 130 and the signal detector 148. In the "reversed path" configuration, the second delivery prism 134 may be replaced by the signal detector 148, eliminating the return optical path through the rotary mount 160. All of these optical coupler arrangements are suitable for very precise stationary to rotary transitions needed for coupling single mode fibers. This is because of the rotational symmetry of the transition about the optical axis, reducing the degrees of freedom for critical alignment and making possible the design of junctions with very low loss (in the order of 0.1 dB) for single mode fibers. Using a single bi-directional optical channel at the stationary-rotary interface coupled with a means to differentiate the light traveling in one direction (delivery) from light traveling in another direction (collection) is a feature not available in the art.

Figure 11:
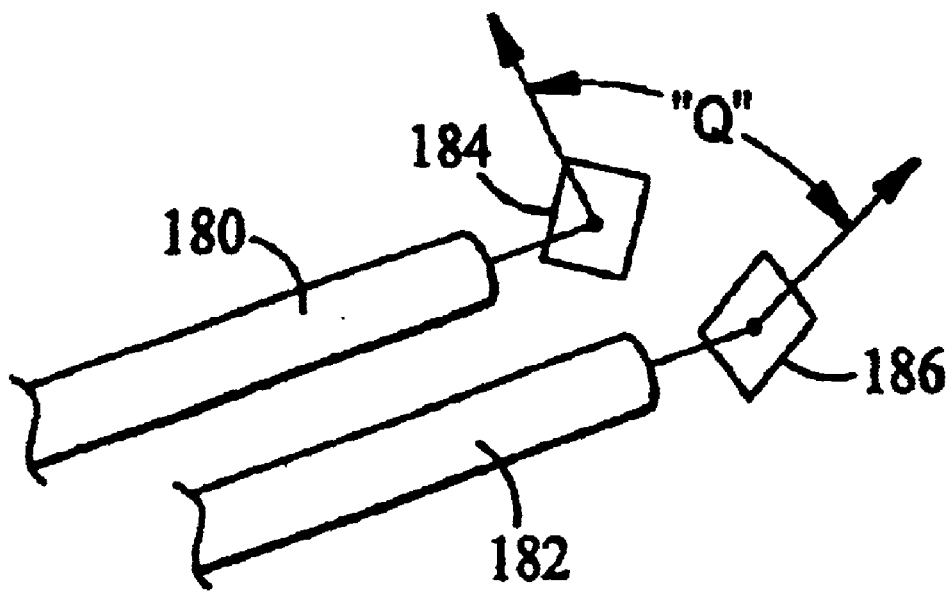
FIG. 11 is a perspective view of independent optical fibers which are angularly separated from one another.
Figure 12:
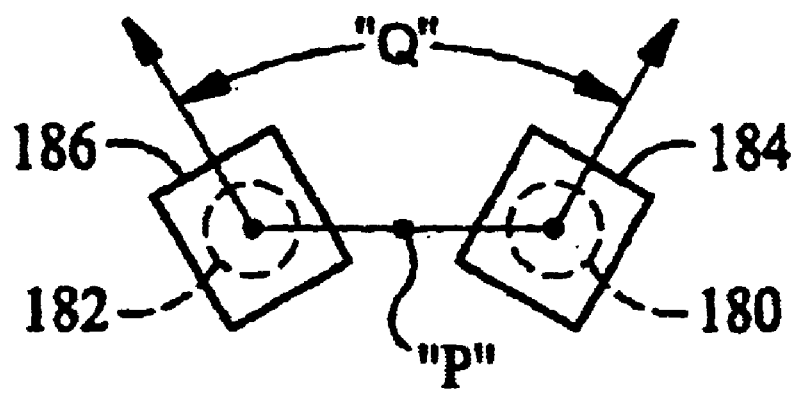
FIG. 12 is an end view of the independent optical fibers and redirectors shown in FIG. 11.

The optical fiber arrangement shown in FIG. 11 presents in a perspective view an independent optical delivery fiber 180 and an independent optical collection fiber 182, each arrangeable within a catheter sheath, not shown for clarity. A re-director 184 or 186 is shown disposed longitudinally adjacent the distal end of each fiber 180 or 182. The redirectors 184 and 186 may for example, be mirror elements, each disposed at an angle "Q" from one another, as measured by the reflective light paths, as may be best seen in FIG. 12. The optical fibers 180 and 182 and the redirectors 184 and 186 may be jointly rotatable about an axis "P" within the catheter, not shown for clarity. The rotation permits circumferential scanning and analysis of a particulate in a medium, which may be a vessel or structure.

The several optical coupler and imaging systems described using the multiple spaced apart optical delivery fiber and optical collection fiber arrangements thus permit a range of optical imaging capabilities of particles that are somewhat different from their suspending medium, including for example, mammalian tissue analysis, chemical analysis and particulate matter in suspension.

We claim:

1. A system for spectroscopic analysis of tissue, the system comprising:
    a catheter defining a lumen extending therethrough;
    an optical delivery fiber arrangement extending through the lumen;
    a delivery re-director disposed at a distal end of the delivery fiber arrangement for directing light from the delivery fiber arrangement against the tissue;
    an optical collection fiber arrangement extending through the lumen;
    a collection re-director disposed at a distal end of the collection fiber arrangement for receiving light from the tissue and directing the received light into the collection fiber arrangement, the collection re-director being separated from the delivery re-director.

2. The system of claim 1, further comprising
    a light source in communication with the delivery fiber arrangement, and
    a signal detector in communication with the collection fiber arrangement.

3. The system of claim 2, further comprising a rotary optical coupler arranged between the light source and the delivery fiber arrangement.

4. The system of claim 2, further comprising a rotary optical coupler arranged between the collection fiber arrangement and the signal detector.

5. The system of claim 2, further comprising a rotary optical coupler arranged to direct light into the delivery fiber arrangement and to receive light from the collection fiber arrangement.

6. The system of claim 5, wherein the rotary optical coupler comprises a beam splitter.

7. The system of claim 2, further comprising an acousto-optic modulator that selectively provides optical communication to one of the collection fiber arrangement and the delivery fiber arrangement.

8. The system of claim 1, wherein the delivery fiber arrangement and the collection fiber arrangement are configured to rotate about a common longitudinal axis within the catheter.

9. The system of claim 1, wherein the delivery fiber arrangement and the collection fiber arrangement have different diameters.

10. The system of claim 1 wherein the delivery fiber arrangement and the collection fiber arrangement form a coiled pair.

11. The system of claim 1, wherein the delivery fiber arrangement comprises a plurality of individual delivery fibers.

12. The system of claim 1, wherein the collection fiber arrangement comprises a plurality of individual collection fibers.

13. The system of claim 1 wherein the delivery fiber arrangement and the receiving fiber arrangement are co-axial with respect to one another.

14. The system of claim 13, further comprising a containing-cladding separating the delivery fiber arrangement and the collection fiber arrangement.

15. The system of claim 14, wherein the containing-cladding longitudinally encloses the delivery fiber arrangement and the collection fiber arrangement.

16. The system of claim 1, wherein the delivery re-director and the collection re-director are spaced apart from one another in a longitudinal direction.

17. The system of claim 1, wherein the delivery re-director and the collection re-director are spaced apart from one another in a radial direction.

18. A method for spectroscopic analysis of a sample of tissue within a vessel, the method comprising:
    inserting a catheter into the vessel;
    placing an optical delivery fiber arrangement through a lumen of the catheter, the optical delivery fiber arrangement having a distal end in optical communication with a delivery re-director for directing light toward the tissue;
    arranging an optical collection fiber arrangement through the lumen, the optical collection fiber arrangement having a distal end in optical communication with a collection re-director for receiving light from the tissue, the collection re-director being spaced apart from the delivery re-director;
    passing light into the delivery fiber arrangement; and
    detecting a signal indicative of light received by the collection fiber arrangement.

19. The method of claim 18, further comprising rotating the collection fiber arrangement and the delivery fiber arrangement about a common axis within the catheter.

20. The method of claim 19, wherein passing light into the delivery fiber arrangement and detecting a signal indicative of light received by the collection fiber comprise connecting the collection fiber arrangement and the delivery fiber arrangement to an optical slip ring.

21. The method of claim 20, further comprising twisting the delivery fiber arrangement and the collection fiber arrangement into a coil about one another.

22. The method of claim 20, further comprising placing the collection fiber arrangement and the delivery fiber arrangement co-axial with one another.

23. The method of claim 20, further comprising selecting the collection and delivery re-directors to be angled fiber members arranged at the distal ends of the collection fiber arrangement and the delivery fiber arrangement respectively.

24. The method of claim 23, further comprising selecting the optical delivery fiber and the optical collection fiber to comprise a common fiber.

25. The method of claim 20, further comprising selecting the optical slip ring to include a rotating coupler in optical communication with the optical collection fiber arrangement and the optical deliver fiber arrangement.

26. The method of claim 20, further comprising selecting the optical slip ring to include an acousto-optical modulator to selectively provide optical communication to one of the deliver fiber arrangement and the collection fiber arrangement.

27. The method of claim 26, further comprising causing the acousto-optical modulator to split a source light beam into a pair of beams in a pair of optical fibers and to recombine a split beam into a common light beam for communication to a detector.

28. The method of claim 20, further comprising selecting the optical slip ring to include a rotatable polarizing beamsplitter in attached rotational conformance with the optical delivery fiber arrangement and the optical collection fiber arrangement.

29. The method of claim 28, further comprising selecting the rotatable polarizing beamsplitter to be in optical communication with a stationary polarizing beamsplitter for communication of a light beam to a signal detector.

30. The method of claim 20, further comprising selecting the delivered light beam and the collected light beam to be non co-linear.

31. A catheter based optical system for generating data indicative of the condition of tissue of a vessel, the system comprising:

a catheter defining a lumen;

an optical delivery fiber arrangement extending through the lumen and configured to rotate about a longitudinal axis of the catheter;

a delivery re-director in optical communication with the optical delivery fiber arrangement, the delivery re-director disposed at a distal end of the optical delivery fiber arrangement for directing light against the tissue;

an optical collection fiber arrangement extending through the lumen and configured to rotate about a longitudinal axis of the catheter, the optical collection fiber arrangement having a diameter that is different from a diameter of the optical delivery fiber arrangement;

a collection re-director in optical communication with the optical collection fiber arrangement, the collection re-director disposed at a distal end of the optical collection fiber arrangement for receiving light from the tissue; the collection re-director and the delivery re-director being longitudinally spaced apart from one another;

a light source in communication with the delivery fiber arrangement;

a signal detector in communication with the collection fiber arrangement for receiving and presenting the data, and a rotary optical coupler disposed between the light source and the delivery fiber arrangement.

32. The system of claim 31, wherein the rotary optical coupler is disposed between the collection fiber arrangement and the signal detector.

33. A method of generating data indicative of a condition of tissue, the method comprising:

inserting, into a catheter, an optical delivery fiber having a distal end coupled to a delivery re-director, inserting, into the catheter, an optical collection fiber having a distal end coupled to a collection re-director separated from the delivery re-director;

attaching a rotary optical pickup to proximal ends of each of the fibers to provide optical communication therewith;

attaching a light source to the rotary optical pickup to provide optical communication between the light source and the delivery re-director;

inserting the catheter into a vessel;

energizing the light source to provide light through the delivery fiber to the delivery re-director and onto the tissue;

collecting light from the tissue into the collection re-director;

receiving the collected light through the rotary optical pickup; and directing the received light into a signal detector for analysis of the tissue.

34. The method of claim 33, further comprising circumferentially scanning the vessel by rotating the delivery fiber and the collection fiber about a common axis.

35. The method of claim 33, further comprising spacing the collection and delivery re-directors apart by a longitudinal distance.

36. The method of claim 35, further comprising adjusting the longitudinal distance between the collection and delivery re-directors by an adjustment arrangement at the proximal end of the catheter.

37. The method of claim 33, further comprising spacing the collection and delivery re-directors apart by a radial distance.

38. The method of claim 33, further comprising positioning the delivery fiber and the collection fiber to be co-axial.

39. The method of claim 38, further comprising placing a containment layer between the delivery fiber and the collection fiber to prevent optical light exchange therebetween.

* * * * *